United States Patent
Bissah et al.

(10) Patent No.: US 8,263,678 B2
(45) Date of Patent: Sep. 11, 2012

(54) COMPOSITIONS FOR REPELLING FLUID AND USES THEREOF

(75) Inventors: Kofi A. Bissah, Somerset, NJ (US); Ricardo De Oliveira, New Hope, PA (US); Saurabh Desai, Somerset, NJ (US); Joseph J. LiBrizzi, Hillsborough, NJ (US); Saroja Narasimhan, Monmouth Junction, NJ (US); Thong Nguyen, Vestal, NY (US); Shoba Pillai, Feasterville, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 349 days.

(21) Appl. No.: 12/641,606

(22) Filed: Dec. 18, 2009

(65) Prior Publication Data

US 2011/0152398 A1 Jun. 23, 2011

(51) Int. Cl.
*A61K 8/37* (2006.01)
*A61K 31/215* (2006.01)
*C08K 5/10* (2006.01)
*C08K 5/101* (2006.01)
*C08L 83/06* (2006.01)

(52) U.S. Cl. ........ 523/105; 524/261; 524/315; 524/588; 524/731; 514/506; 424/70.12

(58) Field of Classification Search .................. 523/105; 524/261, 315, 588, 731; 514/506; 424/70.12
See application file for complete search history.

(56) References Cited

U.S. PATENT DOCUMENTS

| | | | |
|---|---|---|---|
| 5,412,004 A | 5/1995 | Tachibana | |
| 5,672,339 A | 9/1997 | Soyama et al. | |
| 5,811,487 A | 9/1998 | Schulz, Jr. | |
| 5,837,793 A | 11/1998 | Harashima | |
| 5,880,210 A * | 3/1999 | Schulz et al. | 524/731 |
| 6,200,964 B1 | 3/2001 | Singleton | |
| 6,384,023 B2 | 5/2002 | Singleton | |
| 2003/0049212 A1 | 3/2003 | Robinson | |
| 2005/0095210 A1 | 5/2005 | Mattai et al. | |
| 2006/0013792 A1* | 1/2006 | Fontaine et al. | 424/70.12 |
| 2006/0159645 A1 | 7/2006 | Miller | |
| 2006/0257346 A1 | 11/2006 | Mohammadi et al. | |
| 2007/0128233 A1 | 6/2007 | Lu et al. | |
| 2008/0118538 A1* | 5/2008 | Hasegawa et al. | 424/401 |
| 2008/0145443 A1 | 6/2008 | Langolf et al. | |
| 2008/0300561 A1 | 12/2008 | Stridfeldt et al. | |

FOREIGN PATENT DOCUMENTS

| | | |
|---|---|---|
| WO | 99/48472 A1 | 9/1999 |
| WO | 00/06114 A1 | 2/2000 |
| WO | 2006/041764 A1 | 4/2006 |

OTHER PUBLICATIONS

In the USPTO U.S. Appl. No. 12/641,635, the Restriction Requirement dated Apr. 29, 2011.
In the USPTO U.S. Appl. No. 12/641,635, the Non-Final Office Action dated Apr. 29, 2011.
In the USPTO U.S. Appl. No. 12/641,635, the Final Office Action dated Jan. 19, 2012.
European Search Report dated Nov. 17, 2011 for corresponding EP Appln. No. 10252137.4.

* cited by examiner

*Primary Examiner* — Michael Pepitone

(57) ABSTRACT

Provided are compositions for repelling fluids comprising a volatile liquid carrier, a powder-feel agent and less than 5 weight % of an ester selected from the group consisting of formula I, formula II, formula III, and combinations of two or more thereof:

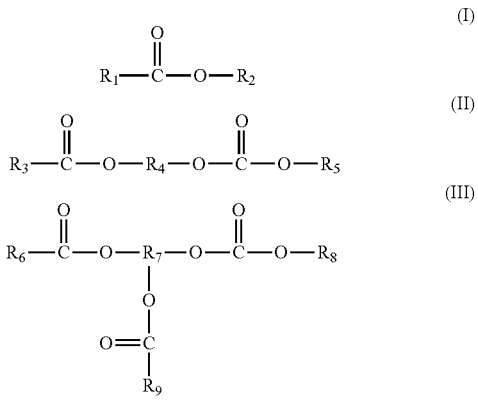

wherein $R_1$, $R_2$, $R_3$, $R_5$, $R_6$, $R_8$ and $R_9$ are independently linear or branched, substituted or unsubstituted, saturated or unsaturated, $C_3$-$C_{22}$ alkyl or alkenyl groups, $R_4$ is a linear or branched, substituted or unsubstituted, saturated or unsaturated, $C_3$-$C_{22}$ alkylene or alkenylene moiety, and $R_7$ is a linear or branched, substituted or unsubstituted, saturated or unsaturated $C_3$-$C_{22}$ moiety, the composition being substantially anhydrous. Also provided are methods of improving dryness and/or comfort associated with the intimate area, as well as, kits comprising the composition and an absorbent article.

7 Claims, No Drawings

COMPOSITIONS FOR REPELLING FLUID AND USES THEREOF

FIELD OF THE INVENTION

This invention relates to compositions for repelling fluid from a surface, in particular a surface of the human body, and methods of use thereof The compositions of the present invention comprise a volatile carrier, a powder-feel agent, and an ester, and are useful, for example, in those areas of the human body which are prone to wetness, such as the intimate area. The compositions of the present invention further tend to aid in preventing odor, skin irritation and chafing associated with exposure to moisture or fluid.

DESCRIPTION OF THE RELATED ART

The intimate area and other surfaces of the body which come in regular contact with fluid can be a source of discomfort and embarrassment in both men and women. Such discomfort and embarrassment may be associated, for example, with adults that suffer from incontinence, and the regular monthly cycles of women during their reproductive years. In both these cases, the discomfort is generally related to irritation and the feeling of wetness and the embarrassment is usually due to the presence of odor. Also, in children, especially infants, the intimate area can become irritated due to the contact of urine and feces.

To overcome these issues, products have been developed which either absorb fluids or wick the fluid away from the body. Examples of such types of products include sanitary production articles, diapers and incontinent products. Over the years, several improvements have been made to such products to aid in absorbing or wicking fluid, for example, superabsorbent material has been added to the constructions, new materials have been developed for the cover layer, transfer layers added to help wick the fluid into the absorbent layers. Additionally, odor control agents have been incorporated to absorb or mask the odor. Inclusion of fragrances may also add additional odor control. All these improvements are based on an external absorbent product which wicks away the fluid or moisture.

Additionally, people for years have used products such as zinc oxide, oil or petrolatum to repel fluid from their skin. These products, while performing quite well at providing a water-proof barrier also left an undesirable sticky feel to the skin.

Examples of other compositions designed to overcome the sticky feel can be found in U.S. Pat. Nos. 6,200,964 and 6,384,023 (both to Singleton et al.) and US 20060159645 (Miller et al.). These references all use a volatile liquid and a silicone polymer.

Nevertheless, applicants have recognized the need for compositions that are more effective at repelling fluid from a surface, such as the surface of a human body than prior compositions, and preferably overcome the sticky feel associated with prior compositions as well.

SUMMARY OF THE INVENTION

The present invention relates to compositions which repel moisture or fluid from a surface, in particular a surface of the human body, more effectively, and in preferred embodiments, further provide a lubricious coating to the surface. According to one embodiment, the present invention provides a composition comprising a volatile cyclic silicone carrier, a silicone-based powder-feel agent, and an ester selected from the group consisting of compounds of Formula I, Formula II, Formula III, and combinations of two or more thereof:

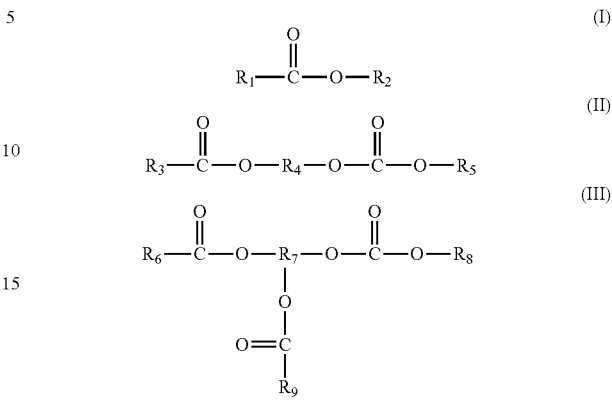

wherein $R_1$, $R_2$, $R_3$, $R_5$, $R_6$, $R_8$ and $R_9$ are independently linear or branched, substituted or unsubstituted, saturated or unsaturated, $C_3$-$C_{22}$ alkyl or alkenyl groups, $R_4$ is a linear or branched, substituted or unsubstituted, saturated or unsaturated, $C_3$-$C_{22}$ alkylene or alkenylene moiety, and $R_7$ is a linear or branched, substituted or unsubstituted, saturated or unsaturated, $C_3$-$C_{22}$ moiety, the composition being substantially anhydrous and the ester present in an amount of about 5% or less.

In another aspect, the invention relates to a method of applying to a surface of a human body a composition comprising a volatile cyclic silicone carrier, a silicone-based powder-feel agent, and an ester.

In another aspect, the invention relates to an absorbent article system comprising an absorbent article and a composition comprising a volatile cyclic silicone carrier, a silicone-based powder-feel agent, and an ester, said absorbent article and composition for application to the intimate area of a human body.

In still another aspect, the invention relates to a method of applying an absorbent article system to the intimate area of a human body comprising applying a composition of the present invention and an absorbent article to the intimate area of a human body such that the composition is in contact with a surface of the intimate area of the body and the absorbent article covers at least a portion of such surface and at least a portion of the composition in contact therewith.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

All percentages listed in this specification are percentages by weight, unless otherwise specifically mentioned.

As used herein, the term "intimate area" shall mean the area near or between the thighs, including the crotch area of a human where body exudates, such as urine, feces, vaginal discharge, menstrual fluid, and the like, may be present. The intimate area shall also include the breasts. The intimate area is typically covered by undergarments or absorbent articles. As used herein the term "absorbent articles" includes articles such as diapers (infant and adult), sanitary napkins, shields, pantyliners, and the like.

The composition of the present invention contains at least three components: a volatile cyclic silicone, a silicone-based powder-feel agent and an ester selected from the group consisting of compounds of Formula I, Formula II, Formula III, and combinations of two or more thereof:

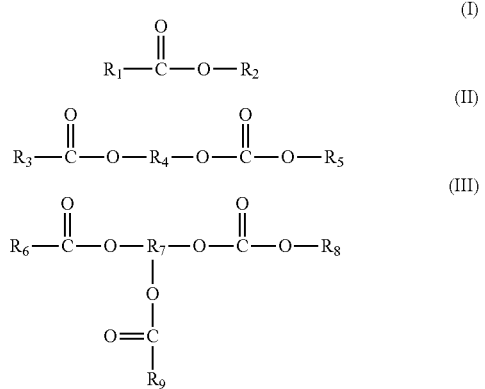

wherein $R_1$, $R_2$, $R_3$, $R_5$, $R_6$, $R_8$ and $R_9$ are independently linear or branched, substituted or unsubstituted, saturated or unsaturated, $C_3$-$C_{22}$ alkyl or alkenyl groups, $R_4$ is a linear or branched, substituted or unsubstituted, saturated or unsaturated, $C_3$-$C_{22}$ alkylene or alkenylene moiety, and $R_7$ is a linear or branched, substituted or unsubstituted, saturated or unsaturated, $C_3$-$C_{22}$ moiety, the composition being substantially anhydrous and the ester present in an amount of about 5% or less.

It has surprisingly been found that application of preferred embodiments of the composition results in a greater repulsion of fluid from the body than previously seen by other comparable compositions. This benefit is demonstrated by the measurement of the contact angle of water placed on a surface that has been treated with the composition in accord with the Contact Angle Test as described herein below. Applicants have discovered unexpectedly, that compositions of the present invention tend to exhibit a contact angle of 90° or greater. In certain preferred embodiments, the compositions exhibit a contact angle of 91° or greater and more preferably 92° or greater. In certain particularly preferred embodiments, the compositions exhibit a contact angle of 93° or greater.

Applicants have further recognized that in addition to unexpected fluid repellency, the compositions of the present invention may further be used on the body to deliver an aesthetically pleasing feel to the skin. Upon application to the skin, the composition delivers a "powdery" feel that is pleasing to the user and yet continues to deliver the benefit of lubrication and slip between the skin surface and other surfaces such as other skin surfaces or external clothing.

Applicants have also measured the Body Dryness Index associated with compositions and uses of the present invention in accord with the test described herein below. Applicants have discovered that compositions of the present invention tend to exhibit a Body Dryness Index of greater than 125. In certain preferred embodiments, the compositions exhibit a Body Dryness Index of about 140 or greater and more preferably about 160 or greater. In certain particularly preferred embodiments, the compositions exhibit a contact exhibit a Body Dryness Index of about 200 or greater, more preferably about 300 or greater.

Any suitable volatile cyclic silicone carrier may be used in the present invention. As used herein the term "volatile" refers to those liquids that have a measurable vapor pressure at ambient temperature. Examples of suitable volatile cyclic silicone carriers include cyclomethicones of the formula:

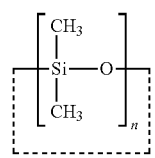

wherein n=3 to 6. Examples of certain preferred volatile cyclic silicone carriers include decamethylcyclopentasiloxane, dodecamethylcyclohexasiloxane, and the like. A particularly preferred volatile cyclic silicone is decamethylcyclopentasiloxane. A variety of commercially available volatile, cyclic polydimethylsiloxanes include: Dow Corning DC 244 and DC 344 fluids (cyclotetrasiloxanes) and DC 245 and DC 345 (cyclopentasiloxanes) manufactured by Dow Corning, Midland Mich.; Volatile Silicone 7158, 7207 and 7349 manufactured by Momentive Performance Materials, Tarrytown, N.Y. and KF9937 and KF9945 manufactured by Shin-Etsu Silicones.

Any material that is capable of delivering a "powdery" feel when released onto the skin may be used in the present invention as a powder-feel agent. Suitable powder-feel agents include a variety of silicone polymers, gels, gums, particulate materials, combinations of two or more thereof, and the like.

Examples of silicone polymers useful as powder-feel agents in the present invention include crosslinked siloxane (e.g., dimethicone or dimethicone derivatives) copolymers such as stearyl methyl-dimethyl siloxane copolymer (Gransil SR-CYC, available from Grant Industries, Elmwood Park, N.J.); dimethicone/vinyldimethicone crosspolymers; Polysilicone-11 (i.e., a crosslinked silicone rubber formed by the reaction of vinyl terminated silicone and methylhydrodimethyl siloxane in the presence of cyclomethicone), cetearyl dimethicone/vinyl dimethicone crosspolymer (i.e., a copolymer of cetearyl dimethicone crosslinked with vinyl dimethyl polysiloxane), dimethicone/phenyl vinyl dimethicone crosspolymer (i.e., copolymer of dimethylpolysiloxane crosslinked with phenyl vinyl dimethylsiloxane), and dimethicone/vinyl dimethicone crosspolymer (i.e., copolymer of dimethylpolysiloxane crosslinked with vinyl dimethylsiloxane). More preferably, the compositions useful in the method of this invention include silicone elastomer blends containing dimethicone/vinyldimethicone crosspolymers (such as those made by Dow Corning), dimethicone, cyclopentasiloxane, trisiloxane, dimethicone and hydrophobically-modified silica.

The silicone polymers may be of any suitable molecular weight. In certain preferred embodiments, the polymers have a weight average molecular weight in excess of 10,000 (e.g., between about 10,000 and 10,000,000).

Examples of suitable silicone gels include the following which are also available commercial from Grant Industries by the indicated tradename: cyclomethicone (and) polysilicone- 11 (Gransil GCM5), cyclotetrasiloxane (D4) (and) petrolatum (and) polysilicone-11 (Grangil PS-4), cyclopentasiloxane (D5) (and) petrolatum (and) polysilicone-11 (Gransil PS-5), cyclopentasiloxane(D5) (and) dimethicone (and) polysilicone-11 (Gransil DMCM-5), cyclotetrasiloxane (D4) (and) dimethicone (and) polysilicone-11 (Gransil DMCM-4), polysilicone-11 (and) isododecane (Gransil IDS), and cyclomethicone (and) polysilicone-11 (and) petrolatum (and) phytosphingosine (Gransil SPH). Other examples of such gels, available from General Electric, include cyclopentasiloxane (and) dimethicone/vinyl dimethicone crossploymer (SFE839). In general, the compositions set forth in U.S. Pat. Nos. 6,200,964 and 6,384,023, which are hereby incorporated herein by reference, are suitable for use in the methods of this invention.

Suitable silicone gels include silicone elastomer gels. The elastomer chemically is a crosslinked, 3-dimensional network of intertwined silicone polymers that swell in the presence of a carrier. Elastomers are not soluble in the carrier but swollen in the carrier. Typically the "effective" carrier solvent is a low molecular weight species that can migrate into the network. The crosslinking density of the elastomer can affect the "swelling" efficiency; generally, lower crosslinking density favors swelling (for a given carrier) and gives a "wetter" feel initially (sometimes could be sticky). Conversely a higher crosslinking density elastomer swells less and gives a "drier" skin feel initially. Most elastomer products dry down to a "powdery" after-feel particularly if the solvent is volatile. One non-limiting example of a suitable class of silicone elastomers is crosslinked organopolysiloxane (or siloxane) elastomers, which are generally described in U.S. patent application publication US2003/0049212A1.

The crosslinked organopolysiloxane elastomers may be categorized as emulsifying or non-emulsifying. "Emulsifying," as used herein, means crosslinked organopolysiloxane elastomers having at least one polyoxyalkylene (e.g., polyoxyethylene or polyoxypropylene) or polyglycerin moiety. The polyoxyalkylene (e.g., polyoxyethylene or polyoxypropylene) or polyglycerin moiety may serve as the crosslinker within the elastomer. Exemplary emulsifying crosslinked organopolysiloxane elastomers are described in U.S. Pat. Nos. 5,412,004; 5,837,793, and 5,811,487. Suitable emulsifying crosslinked organopolysiloxane elastomers include dimethicone/PEG-10 crosspolymers such as KSG 24; dimethicone/PEG-10 crosspolymers such as KSG 21 and KSG 210; PEG-15/lauryl dimethicone crosspolymers such as KSG 31, KG 32, KSG 33, KSG 310, KG 320, KSG 330; PEG-15/lauryl dimethicone crosspolymers and PEG-10/lauryl dimethicone crosspolymers such as KSG 34 and KSG 340; dimethicone/polyglycerine-3 crosspolymers such as KSG-710; and lauryl dimethicone/polyglycerine-3 crosspolymers such as KSG 810, KSG 820, KSG 830, and KSG 840. Also from Shin-Etsu are Silicone Rubber powder, KMP-400 type, Silicone resin powder, KMP-590, X-52-1631, Hybrid silicone powders, KSP-100, KSP-101 and KSP-300, etc.

"Non-emulsifying" means crosslinked organopolysiloxane elastomers are essentially free of polyoxyalkylene or polyglycerin moieties. Exemplary non-emulsifying crosslinked siloxane elastomers include the CTFA (Cosmetic, Toiletry, and Fragrance Association International Cosmetic Ingredient Dictionary and Handbook, 11.sup.th ed.) designated dimethicone/vinyl dimethicone crosspolymers supplied by a variety of suppliers including Dow Corning (DC 9506), General Electric (SFE 839), Shin Etsu (KSG 15 and 16), and Grant Industries (GRANSIL RPS-NA) and dimethicone/phenyl vinyl dimethicone crosspolymer such as KSG 18 available from Shin Etsu. Other exemplary non-emulsifying crosslinked siloxane elastomer include the CTFA designated dimethicone crosspolymers including Dow Corning. (DC 9040, DC 9041, DC 9045).

Also suitable are high molecular weight silicone gums with linear high molecular polymer "solids (gums)" which are soluble in a carrier and water-insoluble silicones inclusive of non-volatile polyalkyl and polyaryl siloxane gums and fluids, volatile cyclic and linear polyalkylsiloxanes, polyalkoxylated silicones, amino and quaternary ammonium modified silicones, rigid cross-linked and reinforced silicones and mixtures thereof, e.g, Dimethiconol (DC 2-9023 fluid), KF 8018 from Shinetsu which is an amino-modified silicone gum (Aminopropyl Dimethicone) in cyclomethicone.

The smooth soft, silky and powdery feel may also be achieved by using particulate materials. Typically, the particulate materials are free-flowing and solid (i.e., the particles are not hollow).

Suitable organic particulate materials include those available commercially under the tradenames as follows: those made of polymethylsilsesquioxane (e.g., Tospearl 145A available from GE Toshiba Silicone Co., Ltd.), polyamide (e.g., nylon-12 and Orgasol 2002D Nat CO5 available from Atofina), polyolefines (e.g., Microthene FN510-00 available from Equistar), polyacrylates (e.g., ethylene acrylate copolymer, sold under the name FloBead EA209 available from Kobo), polymethacrylates (PMMA) (e.g., Micropearl M 100 available from Seppic), polystyrene (e.g., Dynospheres available from Dyno Particles), polytetrafluoroethylene (PTFE), polyurethanes, starch and starch derivatives, composite particles, and mixtures thereof Copolymers derived from monomers of the aforementioned materials can also be used. The aforementioned polymers derived from carboxylic acid containing monomer further include ester and salts of the monomers.

Inorganic materials for improving skin feel include natural minerals such as mica, talc, and sericite, synthetic mica, synthetic sericite, plate-formed titanium oxide, plate-formed silica, plate-formed aluminum oxide, boron nitride, barium sulfate, plate-formed titania-silica composite oxide, and bismuth oxychloride. Further these inorganic particles comprising those described above as a base material and one or more inorganic oxides coating the base material such as titanium oxide, aluminum oxide, iron oxide, silicon dioxide, cerium oxide, and zirconium. The pure titanium or zinc oxides pigments may be coated with compounds such as amino acids such as lysine, silicones, lauroyl, collagen, polyethylene, lecithin and ester oils. The inorganic particles may be resin coated as cited in US patent application 2003/0171475. The resin is preferably one or more selected from the group consisting of polyurethane, a styrene-but adiene copolymer, an acrylonitrile-butadiene copolymer, a silicone-based elastomer, and a polyolefin-based elastomer.

According to certain preferred embodiments, the powder-feel agent is preferably a silicone-based powder feel agent such as a silicone polymer, silicone gels, silicone gums, hydrophobically-modified silica, combinations thereof, and the like. Preferred silicone-based powder feel agents include silicone elastomer blends and hydrophobic silica blends, combinations of two or more thereof, and the like.

Any suitable amounts of powder-feel agents may be used in the present invention. In certain embodiments, the powder feel agent is present in the composition in an amount of about 65% or less by weight of the total composition. In certain preferred embodiments, the powder feel agent is present in an amount of from about 5% to about 65%, more preferably from about 8% to about 65%, more preferably from about 8% to about 60%, more preferably from about 8% to about 40%, and even more preferably from about 8% to about 30% by weight of the total composition.

Suitable esters for use in the present invention include those of Formula I, Formula II, Formula III:

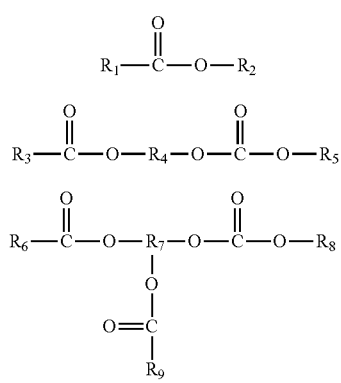

wherein $R_1$, $R_2$, $R_3$, $R_5$, $R_6$, $R_8$ and $R_9$ are independently linear or branched, substituted or unsubstituted, saturated or unsaturated, $C_3$-$C_{22}$ alkyl or alkenyl groups, $R_4$ is a linear or branched, substituted or unsubstituted, saturated or unsaturated, $C_3$-$C_{22}$ alkylene or alkenylene moiety, and $R_7$ is a linear or branched, substituted or unsubstituted, saturated or unsaturated, $C_3$-$C_{22}$ moiety. In certain preferred embodiments the ester of Formula I, Formula II, or Formula III have a viscosity ranging from about 10 to 1,000,000 centipoise at 25° C.

Examples of monoester oils of Formula I that may be used in the compositions of the invention include, but are not limited to, hexyldecyl benzoate, hexyl laurate, hexadecyl isostearate, hexydecyl laurate, hexyldecyl octanoate, hexyldecyl oleate, hexyldecyl palmitate, hexyldecyl stearate, hexyldodecyl salicylate, hexyl isostearate, butyl acetate, butyl isostearate, butyl oleate, butyl octyl oleate, cetyl palmitate, ceyl octanoate, cetyl laurate, cetyl lactate, octyl isonoanoate, isostearyl isononanoate, isononyl isononanoate, cetyl isononanoate, cetyl stearate, stearyl lactate, stearyl octanoate, stearyl heptanoate, stearyl stearate, and so on.

Suitable diesters of Formula II that may be used in the compositions of the invention are the reaction product of a dicarboxylic acid and an aliphatic or aromatic alcohol, or a monocarboxylic acid and an aliphatic or aromatic alcohol containing at least two hydroxyl groups. Preferably, one or more of the acid or alcohol is a fatty acid or alcohol, i.e. contains 3-22 carbon atoms. The dicarboxylic acid may also be an alpha hydroxy acid. Examples of diester oils that may be used in the compositions of the invention include diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisopropyl adipate, diisostearyl dimer dilinoleate, disostearyl fumarate, diisostearyl malate, isononyl isononanaote, isohexadecyl stearate, and so on.

Suitable triesters of Formula III comprise the reaction product of a tricarboxylic acid and an aliphatic or aromatic alcohol, or the reaction of an aliphatic or aromatic alcohol having three or more hydroxyl groups with mono-or dicarboxylic acids. Preferably, one or more of the acid or alcohol is a fatty acid or alcohol containing 3 to 22 carbon atoms. Examples of triesters include triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate, tridecyl cocoate, tridecyl isononanoate, and so on.

In certain preferred embodiments, the ester of the present invention is selected from the group consisting of octyl isononanoate, isopropyl palmitate, butyl stearate, diisopropyl adipate, triisostearyl citrate, and combinations of two or more thereof In certain more preferred embodiments, the ester is selected from the group consisting of octyl isononanoate, isopropyl palmitate, butyl stearate, and combinations of two or more thereof. In certain more preferred embodiments, the ester comprises octyl isononanoate.

The ester selected from the group consisting of esters of Formula I, Formula II, Formula III, and combinations of two or more thereof may be present in the compositions of the invention in an amount of 5% or less by weight based on the total weight of composition. In certain preferred embodiments, the ester is present in an amount of from about 0.5 to about about 4.5%, more preferably from about 1 to about 4%, more preferably from about 2-4%, and even more preferably from about 2-3%.

In certain preferred embodiments, the composition is substantially anhydrous. As used herein, the term "substantially anhydrous" means that the composition contains less than 5% w/w water. In more preferred embodiments, the composition contains less than 3%, more preferably less than 2%, more preferably less than 1%, more preferably less than 0.5% w/w water. In certain preferred embodiments, the substantially anhydrous composition is an anhydrous composition (free of water).

The invention features a method of applying a cosmetic composition suitable for application to the skin, e.g., in the intimate area such as the perineum, under the breasts or on the thighs, of a subject in association with a cosmetically acceptable carrier. The individual components of the carrier are numerous and varied, but are also well known to one skilled in the art. In one aspect, the carrier comprises one or more of the members selected from the group consisting of acidifying agents, alkalizing agents, aerosol propellants, antimicrobial agents, antioxidants, buffering agents, chelating agents, coloring additives, dermatologically active agents, dispersing agents, emollients, emulsifying agents, humectants, fragrances, masking agents, preservatives, sugars, sunscreen agents, surfactants, suspending agents, thickening agents, an vehicles. These ingredients are discussed below. Examples of these agents are listed below as well as in the International Cosmetic Ingredient Dictionary and Handbook, eds. Wenninger and McEwen (The Cosmetic, Toiletry, and Fragrance Assoc., Washington, D.C., 7.sup.th Edition, 1997) (hereinafter "ICT Handbook").

Acidifying and alkalizing agents are preferably added to obtain the desired pH of the composition. Examples of acidifying agents included acetic acid, citric acid, glacial acetic acid, malic acid, and proprionic acid. Examples of alkalizing agent include edetol, potassium carbonate, potassium hydroxide, sodium borate, sodium carbonate, and sodium hydroxide. Other acidifying and alkalizing agents are listed on page 1653 of the ICT Handbook.

Aerosol propellants are used when the composition is to be administered as an aerosol under pressure. Examples of aerosol propellants include halogenated hydrocarbons such as dichlorodifluoromethane, dichlorotetrafluoroethane, and trichloromonofluoromethane, nitrogen, and volatile hydrocarbons such as butane, propane, isobutane, or mixtures thereof. Other propellants are listed on page 1655 of the ICT Handbook.

Anti-microbial agents are used when the area that the composition is to be applied is prone to microbial infection, e.g., by bacteria, fungal, or protozoa. Examples of such agents include benzyl alcohol, chlorobutanol, phenylethyl alcohol, phenylmercuric acetate, potassium sorbate, and sorbic acid, benzoic acid, butyl paraben, ethyl paraben, methyl paraben, propyl pareben, and sodium benzoate. Other anti-microbial agents are listed on page 1612 of the ICT Handbook.

Antioxidants are used to protect ingredients of the composition from oxidizing agents that are included within or come in contact with the composition. Examples of antioxidants include water.soluble antioxidants such as ascorbic acid, sodium sulfite, metabisulfite, sodium bisulfite, sodium formaldehyde, sulfoxylate, isoascorbic acid, isoascorbic acid, cysteine hydrochloride, 1,4-diazobicyclo-(2,2,2)-octane, and mixtures thereof. Examples of oil-soluble antioxidants include ascorbyl palmitate, butytlated hydroxyanisole, butylated hydroxytoluene, potassium propyl gallate, octyl gallate, dodecyl gallate, phenyl-alpha-napthyl-amine, and tocopherols such as alpha-tocopherol. Other antioxidants are listed on pages 1612-13 of the ICT Handbook.

Coloring additives are used to add color to the composition. Examples of such coloring additives include titanium dioxide, yellow iron oxide, red iron oxide, black iron oxide, caramel, carmine, fluorescein derivatives, methoxsalen, trioxsalen, carbon black, azo dyes, anthraquinone dyes, blue azulenes, guajazulene, chamuzulene, erythrosin, bengal rose, phloxin, cyanosin, daphinin, eosin G, cosin 10B, and Acid Red 51. Other coloring agents are listed on pages 1628-30 of the ICT Handbook.

Dermatologically active agents include agents for treating wound healing, inflammation, acne, psoriasis, cutaneous aging, skin cancer, impetigo, herpes, chickenpox, dermatitis, pain, itching, and skin irritation. Examples of such dermatologically active agents include hydrocortisone, dexamethasone, panthenol, phenol, tetracycline hydrochloride, yeast, hexylresorcinol, lamin, kinetin, betamethagone, triamcinolone, fluocinolone, methylprednisolone, retinoids such as retinol and retinoic acid, dapsone, sulfasalazine, resorcinol, salicylic acid, benzoyl peroxide, erythromycin-benzoyl peroxide, erythromycin, clindamycin, mupirocin, griseofulvin, azoles such as miconazole, econazole, itraconazole, fluconazole, and ketoconazole, ciclopirox, allylamines such as naftifine and terfinafine, acyclovir, famciclovir, valacyclovir, benzocaine, lidocaine, dibucaine, pramoxine hydrochloride, methyl salicylate, camphor, menthol, resocinol, and vitamins such as tocopherol, tocopheryl acetate, pentothenic acid, ascorbic acid, biotin, and retinoids such as retinol, retinoic acid, retinal, retinyl acetate, and retinyl palmitate, .alpha.-hydroxy acid, a .beta.-hydroxy acid, or poly-hydroxy acid such as glycolic acid, lactic acid, citric acid, malic acid, and azaleic acid, and sunless tanning agents such as 1,3-dihydroxyacetone and 1,3,4-trihydroxy-2-butanone(erythulose).

Examples of dispersing and suspending agents include quarternium-18 hectorite, polyhydroxy stearic acid, poligeenan and silicon dioxide. Other dispersing and suspending agents are listed on page 1690-91 of the ICT Handbook.

Emollients are agents that soften and smooth the skin. Examples of emollients include hydrocarbon oils and waxes (e.g., natural and synthetic waxes) such as mineral oil, petrolatum, microcristaline wax, polyethylene, triglyceride esters such as those of castor oil, cocoa butter, safflower oil, cottonseed oil, corn oil, olive oil, cod liver oil, almond oil, avocado oil, palm oil, sesame oil, squalene, and soybean oil, acetylated monoglycerides, ethoxylated glycerides, fatty acids, alkyl esters of fatty acids, alkenyl esters of fatty acids, fatty alcohols, fatty alcohol ethers, ether-esters, lanolin and derivatives of lanolin, polyhydric alcohol esters, wax esters such as beeswax, vegetable waxes, phospholipids, and sterols. Other emollients are listed on pages 1656-61 of the ICT Handbook.

Emulsifying agents are used for preparing emulsions of the present invention. Examples of emulsifying agents used for preparing silicone-in-oil, or oil-in-silicone emulsions include cyclomethicone (and) dimethicone copolyol, dimethicone copolyol, cetyl dimethicone copolyol, Humectants are agents that promote the retention of moisture, e.g., moisturizers. Examples of humectants include sorbitol, matricaria extract, aloe barbadensis gel, glycerin, glycereth 5 lactate, glycereth 7 triacetate, glycereth 7 diisononoate, hexanetriol, hexylene glycol, propylene glycol, dipropylene glycol, alkoxylated glucose, D-panthenol, 1-2-pantandiol, 2-methyl-1,3-propanediol, and derivatives thereof, and hyaluronic acid. Other humectants are listed on pages 1661-62 of the ICT Handbook.

Examples of fragrances include peppermint, rose oil, rose water, aloe vera, clove oil, menthol, camphor, eucalyptus oil, and other plant extracts. Certain fragrances may require a solubilizer, e.g., PPG-5-ceteareth-20. To eliminate certain odors from compositions, masking agents may be used. An example of a masking agent includes ethylene brassylate. Other fragrances and masking agents are listed on pages 1639-40 of the ICT Handbook.

Preservatives are used to protect the composition from degradation. Examples of preservatives include liquipar oil, phenoxyethanol, methyl paraben, propyl paraben, butyl paraben, isopropyl paraben, isobutyl paraben, dieizolidinyl urea, imidazolidinyl urea, diazolindyl urea, benzalkonium chloride, benzethonium chloride, phenol, and mixtures thereof (e.g., liquipar oil). Other preservatives are listed on pages 1654-55 of the ICT Handbook. Surfactants are agents used to stabilize multi-component compositions, e.g., used as wetting agents, antifoam agents, emulsifiers, dispersing agents, and penetrants. Examples of surfactants include methyl gluceth 20, decyl polyglucoside, lapyrium chloride, laureth 4, laureth 9, monoethanolamine, nonoxynol 4, nonoxynol 9, nonoxynol 10, nonoxynol 15, nonoxynol 30, poloxalene, polyoxyl 8, 40, and 50 stearate, polysorbate 20, polysorbate 40, polysorbate 60, polysorbate 65, polysorbate 80, and polysorbate 85, sodium lauryl sulfate, sorbitan and its derivatives. Other surfactants are listed on page 1672-90 of the ICT Handbook.

The cosmetically acceptable carrier that may be in a number of different delivery forms, e.g., a spray, mist, aerosol, mousse, semi-solid cream, liquid such as a solution, emulsion, or suspension, lotion, gel, solid such as a powder, adherent stick, flexible mask, self-hardening liquid or gel, or other suitable forms intended to be applied to the skin of a subject (e.g., a human).

The viscosity of the compositions of the present invention may be different dependent upon the type of formulation being prepared, e.g., a liquid formulation will have a lower viscosity than a gel or cream formulation. Typically, the viscosity of liquid formulations of the present invention will range from 5,000 to 25,000 cps. Bulking agents may be used to increase the viscosity of the composition.

The compositions of this invention may be prepared using methodology that is well known by an artisan of ordinary skill (e.g., by using well-known mixing and blending procedures).

The compositions of this invention may be packaged in a container that is well known by an artisan of ordinary skill, e.g., the silicone gel may be packaged in a low density polyethylene tube with a dispensing tip head and the cosmetic foundation of the present invention may be packaged in a glass or plastic bottle. Other types of packaging such as wipes or aerosol are within possible the possible realm for delivery of the composition to the intimate area.

In one aspect of the invention, the composition which contains a volatile liquid carrier, a powder-feel agent and an ester, and has a contact angle of at least 90°, is applied to the intimate area of the human body, preferably to improve dryness by repelling fluid, improving the Body Dryness index, or both. Any suitable steps for application to the intimate area may be used. In certain embodiments, a user may directly transfer the composition from a container to the skin or may place the composition in his or her hand or fingers and transfer the fluid from there to the intimate area. Another method for applying the composition is to place the composition onto an applicator, for example, a wipe, swab, absorbent article, or other article and transfer the composition from such article to the skin. Alternately, the composition may be disposed within an aerosol container or other sprayable form and sprayed directly onto the skin. A variety of other methods of application suitable for use herein will be apparent to one of skill in the art.

In certain preferred embodiments, the application step comprises applying the composition to the perineal area. In other preferred embodiments, the application step comprises applying the composition to a portion of the intimate area to be covered by a diaper. In other preferred embodiments, the application step comprises applying the composition to the breasts.

The method of the present invention may further comprise the step of applying a garment or absorbent article over at least a portion of the intimate area to which a composition of the present invention has been applied. In certain preferred embodiments, the step comprises applying an undergarment over at least a portion of the intimate area to which a composition of the present invention has been applied. In certain other preferred embodiments, the step comprises applying a sanitary napkin, shield, or pantyliner over at least a portion of the intimate area to which a composition of the present invention has been applied In another aspect, the invention relates to a system or kit containing a composition of the present invention and an absorbent article. The composition and absorbent article may be packaged together or separately, preferably they are packaged together. The kit may further include any of a variety of additional absorbent articles, ancillary products, applicators, or the like. Examples of suitable ancillary products include wipes, sanitary napkins, diapers, breast pads, lotions, cleansers, and the like. Suitable applicators may include any article for transferring the composition from its container to the intimate area and/or to a surface of the absorbent article.

In still another aspect, the invention relates to a method of applying an absorbent article system to, and/or improving the comfort associated with the use of an absorbent article in, the intimate area of a human body comprising applying a composition of the present invention and an absorbent article to the intimate area of a human body such that the composition is in contact with a surface of the intimate area of the body and the absorbent article covers at least a portion of such surface and at least a portion of the composition in contact therewith. As will be recognized by one of skill in the art, improved comfort to a user of an absorbent article may include improved comfort at application of the absorbent article, improved comfort from application to use/introduction of fluid to the article, improved comfort after use/introduction of fluid to the absorbent article, or combinations of two or more thereof, as compared to use of the article without a composition of the present invention. Moreover, improved comfort may include beneficial changes to any one or more properties associated with comfort including dryness, irritation and chafing, cleanliness, freshness, sensation of the article and/or fluid, feel associated with wearing and/or use of the article, hot/sweaty/sticky feel, urge to change article, skin feel (e.g. softer, smoother, silkier skin feel), or combinations of two or more thereof.

According to certain preferred embodiments, the methods of the present invention comprise improving any one alone, or combination of two or more, of the following properties/measures: repelling fluid (indicated by Contact Angle), Body Dryness Index, Body Sensory Index, Body Heat Index, and/or sensation of fluid (relatively cool and/or warm fluid). In certain preferred embodiments, the method of improving the comfort comprises increasing repulsion of fluid from the intimate area to the absorbent article. In certain other preferred embodiments, the method of improving comfort comprises increasing the Body Dryness Index associated with the use of the absorbent article.

Any suitable steps for applying both the composition and absorbent article may be used in such method. For example, the composition may be first applied to the intimate area followed by application of the absorbent article such that the article covers at least a portion of the area to which the composition has been applied. In another example, the composition may be applied to the absorbent article and then both composition and article applied to the intimate area such that the composition is in contact with the intimate area and the absorbent article covers at least a portion of the area to which the composition is applied.

EXAMPLES

The following is a description of the manufacture and measure of certain compositions of the present invention and comparative compositions. Other compositions of the invention can be prepared in an analogous manner by a person of ordinary skill in the art.

The following test procedures are used in the Examples, and the following materials are used in certain of such test procedures:

Bodily Fluid Simulating fluid ("BFS fluid") was made of the following mixture to simulate bodily fluids: 49.5% of 0.9% sodium chloride solution (VWR catalog #VW 3257-7), 49.05% Glycerin (Emery 917), 1% Phenoxyethanol (Clariant Corporation Phenoxetol.™) and 0.45% Sodium Chloride (Baker sodium chloride crystal #9624-05).

Vitro-Skin® substrate: testing substrate which mimics the surface properties of human skin available as Vitro-Skin® N-19 manufactured by IMS Inc, ME, USA. In certain tests a "hydrated" Vitro-Skin is used. The hydrated substrate is prepared as follows:

Necessary reagents for making the hydrated solution:
1. 256 g water
2. 44 g glycerin
3. 3 g glydant Step 1: Combine reagents in 500 ml beaker and mix well for about 1 minute Step 2: Remove top shelf of IMS hydration chamber and pour solution into the chamber Step 3: Cut the V-skin into strips and place them onto the top shelf. Do not overlap strips.

Step 4: Place the shelf back into the hydration chamber and seal tightly to prevent drying.

Step 5: Hydrate the skin for 8-24 hours.

Test Procedure for Measuring Contact Angle (CAM)

For each composition for which a CAM is to measured, a 2 A 2"×2" sample film was created using a Leneta 2A Opacity chart, a BYK Gardner Opacity Drawdown Base, and a BYK Gardner wet film drawdown bar with a thickness of 1.5 mil. The Opacity Drawdown Base was used to hold the opacity chart at a constant position during the drawdown application process. The drawdown process involved placing small amount of composition across the top of the opacity charts and using the Drawdown bar to vertically cover the chart with the composition. This vertically up-down motion was carried out until the composition formed a uniform film over the opacity charts. The charts were then cut into 2"×2" film strips, and weighed on a Mettler Toledo scale.

Advancing contact angles of each sample strip were measured using the Krüss DS 100 Drop Shape Analysis machine. Following the manual instructions of the machine, the angle of inclination on was tilted to 2 degrees; the third syringe was selected; the drop type was changed to sessile drop; and the drop subtype was changed to normal sessile drop. The thickness of the needle was 0.509 mm. BFS fluid was placed in the machine and allowed to flush through the needle for a few minutes in order to remove flush the needle. The drop volume was manually controlled at a rate of 50 µl/minute. With the camera in focus, contact angles of 4 sessile drops were measured on each strip. The sample size of this experiment is 4 (n=4) and Average Contact Angle Measurement (CAM) was recorded.

Test Procedure for Body Dryness Index

For each composition for which a BDI is being measured (each a "test composition"), a 2"×2" sample of hydrated Vitro-Skin® substrate was cut and the weight recorded. This film sample provides a liquid impervious surface and represents the body in this test. The test composition, 0.5 grams thereof, was spread uniformly across the top surface of the film to form a test sample (Gardner Draw with variable thickener was used with 1.5 mil set clearance is used to spread the test composition evenly across the hydrated Vitro-Skin® substrate to form a substantially uniform coated film on the Vitro-Skin® substrate). A control sample with no test composition applied thereto was prepared. All samples are weighed and recorded as initial weights. N=3

Using a Corning Syringe Pump, 10 mL of BFS fluid was dispensed onto the surface of the test samples and control sample. The test samples and control sample were then allowed to rest for 2 minutes. Each film was then tilted at a 45 incline for 1 minute to allow excess fluid to drain off The weights were recorded as final weights N=3.

The Body Dryness Index (BDI) calculation is based on the Body Wetness Index (BWI), which is the residual fluid on the skin (g) divided by the total weight of the fluid dispensed.

$$\text{Body Wetness Index } (BWI) = \frac{\text{residual fluid on skin (g)}}{\text{Total weight of fluid dispensed (g)}}$$

$$\text{Body Dryness Index } (BDI) = \frac{1}{BWI}$$

Test Procedure for Body Sensory Index

The interface between perineal skin and sanitary pad is a high contact area, and the constant interaction of these two surfaces results in much discomfort. Mechanical irritation like frictional abrasion is a significant cause of skin damage. Frictional forces are quantified by µ, the coefficient of friction. High µ values indicate higher friction, and low µ values indicate lower friction. Lubricity (L) is the mathematical inverse of µ. Therefore, a large lubricity signifies high lubrication and low friction. Lubricity measurements can be combined with the Body Dryness Index (BDI) to establish the Body Sensory Index (BSI), a gauge of a woman's perception of her pad. Mathematically, this can be expressed as $$BSI = \frac{\mu}{BDI} = \frac{1}{BDI \times L}$$

Ideally, a woman does not feel and is not bothered by her pad. A low BSI implies the weakest sensation and is thus preferred over high values of BSI.

Experimental: For each composition for which a BSI is being measured (each a "test composition"), a CETR Tribometer instrument was used to measure µ. The CETR Tribometer probe and base were programmed to follow a specific path while under a 50 g load. The probe was to first move 5 mm to the right. Next, the base was programmed to move 10 mm back.

Polyethylene (PE) film was then cut into a 2"×2" sample and securely affixed to a plexiglass base with tape. The CETR Tribometer movement sequence was initiated, and as the probe and base moved across the PE film, values for µ were recorded.

This procedure was repeated using PE film covered by 0.50 g of test composition. The test composition was applied to the PE film using a drawdown bar at a 1.400 mm thickness to ensure an even contact surface.

The inverse of the average µ was taken and this value was used in the equation to calculate the BSI. The BDI of each of the test compositions is also measured and the BSI is calculated using the equation above.

Test Procedure for Body Heat Index

The heat index is a measurement of human-perceived heat and considers both temperature and humidity. It can be expressed as a mathematical relationship of the relative humidity (R) and temperature (T) of a given environment:

$$HI = -42.379 + 2.049015237T + 10.14333127R - 0.22475541TR - 6.83783 \times 10^{-3}T^2 - 5.481717 \times 10^{-2}R^2 + 1.22874 \times 10^{-3}T^2R + 8.5282 \times 10^{-4}TR^2 - 1.99 \times 10^{-6}T^2R^2$$

The perineal area in women is typically high in humidity due to the accumulation of fluids and the occlusive effects of pads and panties. The heat index is consequently very high and conditions are uncomfortable. Therefore, the reduction of both relative humidity and heat index leads to improved comfort.

Experimental: Using a hotplate, a 3"×10" piece of plexiglass was preheated to 38° C. and then removed from further heat. Next, a Stayfree® brand regular maxi pad with cottony cover was attached to a 100% cotton panty and loaded with 3.0 mL of water. There was no water added if the dry test was being carried out.

A 0.50 g composition sample was measured and evenly spread onto a 2"×2" piece of hydrated Vitro-Skin using a spatula. The piece of Vitro-Skin was then laid onto the heated plexiglass and allowed to equilibrate to 33° C. A Digital Humidity Sensor model SHT75 made by Sensirion (Switzerland) was placed directly against the Vitro-Skin so that the measurements reflect only skin conditions. After the relative humidity had stabilized, the pad and panty were positioned directly over the Vitro-Skin. A weighted glass cylinder was placed over the Vitro-Skin, sensor, pad and panty to create a controlled microenvironment.

Test Procedure for Sensation of Fluid

A beaker of cold water was prepared by adding ice and maintaining the temperature at 5-10° C. Four regions (one inch square) are marked on the inside of each forearm of a test subject, and area with little to no visible hair is chosen. Using a pipette, a single drop of cold water was deposited in each of the four regions of one forearm of the subject. The subject is blinded from the dropping of water, that is, subjects do not see the deposition of fluid so that visual cues do not impact their sensation of the water drops. After each drop, the test subject is asked to rate on a scale of 1 to 5 how strongly they feel the drop (5 being the strongest sensation and 1 being no sensation at all). If there is sensation, the subject is asked to indicate whether the drop feels cold or hot.

Then, for each composition to be tested (each a "test composition") a sample of about 0.1 grams of test composition is applied to corresponding regions on the subject's other forearm. Repeat the fluid deposition procedure and ask the test subjects to again rate the sensation on a 1-5 scale. If there is sensation, ask the subject to indicate whether the drop feels cold or hot.

On the next day, prepare a beaker of warm water. Maintain water temperature at 40-45° C. Repeat the entire procedure using warm water.

Comparative Example 1

Contact Angle Testing was performed to determine the contact angle of a series of esters (Repellant Agents) labeled as comparative compositions C1-C5.

TABLE 1

| Example | Ester/ Repellant Agent | INCI Name | Supplier | Location | Contact Angle Measurement |
|---|---|---|---|---|---|
| C1 | HallStar Octyl Isononanoate (Duck Oil) | Octyl isononanoate | HallStar Co | Hackettstown, NJ | 55.0° |
| C2 | HallStar IPP | Isopropyl palmitate | HallStar Co | Hackettstown, NJ | 53.1° |
| C3 | HallStar BST | Butyl stearate | HallStar Co | Hackettstown, NJ | 56.2° |
| C4 | Ceraphyl (DIPA) | Diisopropyl adipate | International Specialty Products | Wayne, NJ | 74.3° |
| C5 | TISC Ester | Triisostearyl citrate | Lubrizol Advanced Materials | Cleveland, OH | 78.6° |

Duck oil is a long chain monoester with two branches. IPP is a long chain monoester with a single chain. BST is a long chain monoester, unbranched. DIPA is a branched diester. TISC is a large, branched triester. All of these esters alone have a contact angle of less than 90°.

Example 1

A base formulation (B1), several inventive examples (E1-E5), and comparative examples (C6-C15) were prepared as described below. The CAM of each was measured and is reported below in Table 3.

A base formulation B1 was prepared using the ingredients of Table 2.

TABLE 2

| Base Formulation (B1) | | | | | |
|---|---|---|---|---|---|
| Function | Trade Name | INCI Name | Supplier | Address | Conc. w/w % |
| Volatilizing Agent | DC 245 Fluid | Decamethylcyclopentasiloxane | Dow Corning Corp. | Midland, MI | 56.57 |
| Powder Feel Agents | USG-103 | Dimethicone/vinyl dimethicone crosspolymer | Shin-Etsu Silicone of America | Akron, OH | 18.18 |
| Bulking Agents | DC 200 Fluid, 350 cSt | Dimethicone | Dow Corning Corp. | Midland, MI | 10.1 |
| Bulking Agents | KF 8018 | Aminopropyl dimethicone | Shin-Etsu Silicone of America | Akron, OH | 7.07 |
| Powder Feel Agents | KSP 100 | Vinyl dimethicone/methicone silsesquioxane crosspolymer | Shin-Etsu Chemical Co. | Tokyo, Japan | 5.05 |

TABLE 2-continued

Base Formulation (B1)

| Function | Trade Name | INCI Name | Supplier | Address | Conc. w/w % |
|---|---|---|---|---|---|
| Powder Feel Agents | Cabosil M5 | Silica | Cabot Corp. | Somerset, NJ | 1.52 |
| Powder Feel Agents | Cabosil TS 610 | Dichlorodimethylsilane | Cabot Corp. | Somerset, NJ | 1.52 |

The ingredients were combined in the order they appear in the table into a glass beaker, stirred with a propeller mixer until the resultant composition was completely uniform. The composition was prepared at room temperature. The CAM of the composition B1 was measured to be 85.6°.

Compositions E1-E5 of the present invention and comparative compositions C6-C16 were made by combining all of the ingredients from B1 and an additional ester (Repellant Agent) as identified, and in the amount as indicated, in Table 4. The general formulations of such compounds were thus as indicated in Table 3.

TABLE 3

| Function | Trade Name | INCI Name | E1-E5 | C6-C10 | C11-C15 |
|---|---|---|---|---|---|
| Volatilizing Agent | DC 245 Fluid | Decamethyl-cyclopentasiloxane | 56.0 | 53.737 | 50.909 |
| Powder Feel Agents | USG-103 | Dimethicone/vinyl dimethicone crosspolymer | 18.0 | 17.273 | 16.364 |
| Bulking Agents | DC 200 Fluid, 350 cSt | Dimethicone | 5.0 | 4.798 | 4.545 |
| Bulking Agents | KF 8018 | Aminopropyl dimethicone | 7.0 | 6.717 | 6.364 |
| Powder Feel Agents | KSP 100 | Vinyl dimethicone/methicone silsesquioxane crosspolymer | 10.0 | 9.596 | 9.091 |
| Powder Feel Agents | Cabosil M5 | Silica | 1.5 | 1.439 | 1.364 |
| Powder Feel Agents | Cabosil TS 610 | Dichlorodimethylsilane | 1.5 | 1.439 | 1.364 |
| Repellant Agent from Table 4 | — | — | 1.0 | 5.0 | 10.0 |

Compositions E1-E5 and C6-C15 were made as follows: the ratios of materials specified in Table 4 were measured out such that the total mixture weight was 100 grams. The Repellant Agents (esters) were added first to the Volatilizing Agents and mixed in a beaker using a propeller mixing blade at 100 RPM for 1-2 minutes. Powder Feel Agents were then added and mixed at 400-500 RPM until there were no visible clumps. CAM was measured for each resultant composition and reported in Table 4.

TABLE 4

| Example | Repellant Agent | Concentration | CAM |
|---|---|---|---|
| B1 | Base Formulation | — | 85.6° |
| E1 | Octyl isononanoate | 1 | 93.6 |
| E2 | HallStar IPP | 1 | 93.6 |
| E3 | HallStar BST | 1 | 93.8 |
| E4 | Ceraphyl (DIPA) | 1 | 93.2 |
| E5 | TISC Ester | 1 | 95.2 |
| C6 | Octyl isononanoate | 5 | 82.0 |
| C7 | HallStar IPP | 5 | 82.9 |
| C8 | HallStar BST | 5 | 83.4 |
| C9 | Ceraphyl (DIPA) | 5 | 84.9 |
| C10 | TISC Ester | 5 | 86.7 |
| C11 | Octyl isononanoate | 10 | 59.3 |
| C12 | HallStar IPP | 10 | 73.5 |
| C13 | HallStar BST | 10 | 79.6 |
| C14 | Ceraphyl (DIPA) | 10 | 80.4 |
| C15 | TISC Ester | 10 | 82.4 |

As illustrated in Table 4, adding less than 5% of the Repellant Agent to the base formulation resulted in a composition having a CAM over 90°. This is a significant and surprising increase over the CAM of the base formulation (B1) or the Repellant Agents alone (see Table 1).

Example 2

Several compositions of the claimed invention (E6-E9) and comparative compositions (C16-C27) were made and the CAM of each tested and reported in Table 5. Each of compositions E6-E9 and C16-C27 were made up of three components: the Volatilizing Agent, Powder Feel Agent, and Repellant Agent (Duck Oil (HallStar Octyl Isononanoate)) as identified, and in the amounts as listed, in Table 5. Such compositions were made as follows: the Repellant Agent was added first to the Volatilizing Agent and mixed in a beaker using a propeller mixing blade at 100 RPM for 1-2 minutes. The Powder Feel Agent was then added and mixed at 400-500 RPM until there were no visible clumps.

TABLE 5

| Comp. | Volatilizing Agent (VA) | INCI | VA Conc. w/w % | Powder Feel Agent (PFA) | PFA Conc. w/w % | RA (Duck Oil - Hallstar) Conc. w/w % | CAM |
|---|---|---|---|---|---|---|---|
| C16 | IDD (Isododecane) | Isododecane | 41.5 | USG 103 | 57.5 | 1 | 78.3° |
| C17 | IDD | Isododecane | 75 | KSP 100 | 24 | 1 | 48.1 |
| C18 | IDD | Isododecane | 91 | TS 610 | 8 | 1 | 83.9 |
| C19 | IDD | Isododecane | 94 | M5 | 5 | 1 | 12.6 |
| C20 | IHD (Isohexadecane) | Isohexadecane | 41.5 | USG 103 | 57.5 | 1 | 77.9 |
| C21 | IHD | Isohexadecane | 75 | KSP 100 | 24 | 1 | 51.2 |
| C22 | IHD | Isohexadecane | 91 | TS 610 | 8 | 1 | 81.4 |
| C23 | IHD | Isohexadecane | 94 | M5 | 5 | 1 | 14.2 |
| C24 | DC 200 (DC 200 5 cST) | Dimethicone | 41.5 | USG 103 | 57.5 | 1 | 71.3 |
| C25 | DC 200 | Dimethicone | 75 | KSP 100 | 24 | 1 | 54.5 |
| C26 | DC 200 | Dimethicone | 91 | TS 610 | 8 | 1 | 85.1 |
| C27 | DC 200 | Dimethicone | 94 | M5 | 5 | 1 | 21.3 |
| E6 | DC 245 | Decamethyl-cyclopentasiloxane | 41.5 | USG 103 | 57.5 | 1 | 92.8 |
| E7 | DC 245 | Decamethyl-cyclopentasiloxane | 75 | KSP 100 | 24 | 1 | 90.5 |
| E8 | DC 245 | Decamethyl-cyclopentasiloxane | 91 | TS 610 | 8 | 1 | 96.4 |
| E9 | DC 245 | Decamethyl-cyclopentasiloxane | 94 | M5 | 5 | 1 | 34.1 |

As illustrated in Table 5, the compositions comprising a volatile cyclic silicone carrier, ester, and certain powder feel agents tended to exhibit significantly higher CAM than comparative compositions. In particular, the compositions of the invention exhibited CAM values above 90°.

Example 3

Four compositions of the claimed invention (E10-E13) and a comparative composition (C28) were made and the CAM of each tested and reported in Table 6. Each of the compositions were made up of three components: the Volatilizing Agent, Powder Feel Agent, and Repellant Agent (Duck Oil) as identified, and in the amounts as listed, in Table 6. The compositions were made in the same manner as E6-E9.

As illustrated in Table 6, compositions comprising a volatile cyclic silicone carrier, ester, and certain powder feel agents tended to exhibit significantly higher CAM than comparative compositions. In particular, the compositions of the invention exhibited CAM values above 90°.

Example 4

Six compositions of the claimed invention (E14-E19) and seven comparative compositions (C29-C35) were made and the CAM of each tested and reported in Table 7. Each of the compositions were made up of three components: the Volatilizing Agent (DC 245, decamethylcyclopentasiloxane), Powder Feel Agent, and Repellant Agent (Duck Oil-Hallstar)

TABLE 6

| Comp. | DC 245 Conc. w/w % | Duck Oil - Hallstar Conc. w/w % | Powder Feel Agent | Characteristics | Conc. | CAM (degrees) |
|---|---|---|---|---|---|---|
| E10 | 41.5 | 1 | USG 103 | High MW silicone elastomer/cross-linked polymer gel in volatile cyclic silicone solvent | 57.5 | 92.8° |
| E11 | 34 | 1 | USG 103 | High MW silicone elastomer/cross-linked polymer gel in volatile cyclic silicone solvent | 65 | 93.8 |
| E12 | 75 | 1 | KSP 100 | High MW silicone cross-linked polymer powder, thickener | 24 | 90.5 |
| E13 | 91 | 1 | TS 620 | Low MW hydrophobic silica, thickener | 8 | 96.4 |
| C28 | 91-94 | 1 | M5 | Low MW untreated silica, thickener | 5-8 | Below 90 | as identified, and in the amounts as listed, in Table 7. The compositions were made in the same manner as E6-E9.

TABLE 7

| Comp. | DC 245 Conc. w/w % | Duck Oil (Conc. w/w %) | Powder Feel Agent | Powder Feel Agent (Conc. w/w %) | CAM |
|---|---|---|---|---|---|
| E14 | 91 | 1 | TS 610 | 8 | 96.4 |
| E15 | 41.5 | 1 | USG 103 | 57.5 | 92.8 |
| E16 | 75 | 1 | KSP 100 | 24 | 90.5 |
| C29 | 94 | 1 | M5 | 5 | 34.1 |
| E17 | 89 | 3 | TS 610 | 8 | 93.2 |
| E18 | 39.5 | 3 | USG 103 | 57.5 | 90.1 |
| C30 | 73 | 3 | KSP 100 | 24 | 76.6 |
| C31 | 92 | 3 | M5 | 5 | 31.8 |
| E19 | 88 | 4 | TS 610 | 8 | 90.4 |
| C32 | 38.5 | 4 | USG 103 | 57.5 | 83.4 |
| C33 | 72 | 4 | KSP 100 | 24 | 53.4 |
| C34 | 91 | 4 | M5 | 5 | 32.1 |
| C35 | 74 | 2 | KSP | 24 | 86.7 |

As illustrated in Table 7, compositions comprising a volatile cyclic silicone carrier, ester, and certain powder feel agents tended to exhibit significantly higher CAM than comparative compositions. In particular, the compositions of the invention exhibited CAM values above 90°.

Example 5

The Body Dryness Index for the base formulation B1 and Examples E1-E5 was measured in accord with the procedure below and is reported in Table 8.

Table 8 represents the volume of test fluid absorbed by the V-skin uncoated or coated with the test composition for certain times. The values were generated by subtracting the initial weight($W_i$) from the final weight($W_f$) for each time period.

TABLE 8

| Sample | $W_f - W_i$ | BDI |
|---|---|---|
| Control (uncoated skin) | | 74 |
| B1 | | 125.0 |
| E1 | 0.006 | 166.7 |
| E2 | 0.007 | 142.9 |
| E3 | 0.005 | 200.0 |
| E4 | 0.003 | 333.3 |
| E5 | 0.003 | 333.3 |

As shown by the above data, surfaces coated with a layer of the test composition containing a repellent agent had a higher BDI that the surface coated with just the control test formulation (no repellent agent).

What is claimed is:

1. A composition comprising 34 to 94 weight percent of a volatile cyclic silicone carrier selected from the group consisting of decamethylcyclopentasiloxane, dodecamethylcyclopentasiloxane, or a combination thereof, from about 5 to about 65 weight percent of a silicone-based powder-feel agent selected from the group consisting of silicone elastomers, hydrophobic silica, or combinations thereof, and an ester selected from the group consisting of octyl isononanoate, isopropyl palmitate, butyl stearate, diisopropyl adipate, triisostearyl citrate, and combinations of two or more thereof, wherein the ester is present in an amount of less than 5 weight percent, the composition being substantially anhydrous.

2. The composition of claim 1 having a Contact Angle of 90° or greater.

3. The composition of claim 1, wherein said cyclic volatile silicone carrier is decamethylcyclopentasiloxane.

4. The composition of claim 1, wherein the powder feel agent comprises a high molecular weight cross-linked silicone elastomer.

5. The composition of claim 1, wherein the powder feel agent comprises a hydrophobic silica particle.

6. The composition of claim 1 wherein the ester is selected from the group consisting of octyl isononanoate, isopropyl palmitate, butyl stearate, and combinations of two or more thereof.

7. The composition of claim 1, wherein the ester is octyl isononanoate.

* * * * *